United States Patent [19]

Grubman

[11] Patent Number: 4,781,709
[45] Date of Patent: Nov. 1, 1988

[54] AIDS-PREVENTING CONDOM SHIELD ARTICLE

[76] Inventor: Mark Grubman, 99-32/ 66 Rd., Rego Park, N.Y. 11374

[21] Appl. No.: 43,050

[22] Filed: Apr. 27, 1987

[51] Int. Cl.⁴ ............................................. A61F 5/44
[52] U.S. Cl. ................................. 604/349; 128/844; 128/859; 128/863
[58] Field of Search ............................. 604/349–353; 2/49 A, 49 R, 87; 128/132 R, 136

[56] References Cited

U.S. PATENT DOCUMENTS

| | | | |
|---|---|---|---|
| 2,591,783 | 4/1952 | Craddock | 604/353 |
| 3,536,066 | 10/1970 | Ludwig | 128/132 R |
| 4,589,408 | 5/1986 | Singer | 128/132 R |
| 4,664,104 | 12/1987 | Jaicks | 604/353 |
| 4,677,696 | 7/1987 | Tanaka | 2/84 |

FOREIGN PATENT DOCUMENTS

| | | | |
|---|---|---|---|
| 1158507 | 12/1983 | Canada | 604/349 |
| 575307 | 7/1924 | France | 604/349 |
| 735179 | 11/1932 | France | 2/49 R |

*Primary Examiner*—C. Fred Rosenbaum
*Assistant Examiner*—J. L. Kruter
*Attorney, Agent, or Firm*—William T. Hough

[57] ABSTRACT

In a preferred embodiment, a condom-like article includes a condom-like closed-end sleeve having at its open end a continuous water-impervious sheet (shield) having a height extending upwardly from the hole at-least about seven or more inches sufficiently to overlay a navel of a male person wearing the condom-sleeve and extending downwardly at-least about two inches or more, there being liquid-catching and retaining cup-like structures at the bottom of the sheet on each of the flat hole-side face of the sheet and of the opposite face, each cup-like structure being positioned and adapted to catch or receive and retain any liquid draining or forced through the lower end, and the sheet further having a handle-structure extending from its flat face at or near the upper end of the sheet, and securing elements for tying or otherwise intermittently mounting the upper end of the sheet onto a mid or upper part of the body of the male wearing the condom-like article, and as a part of a combination, a water impervious mask with mounting mechanism therefor, for intermittently covering the mouth and nose during copulation.

16 Claims, 2 Drawing Sheets

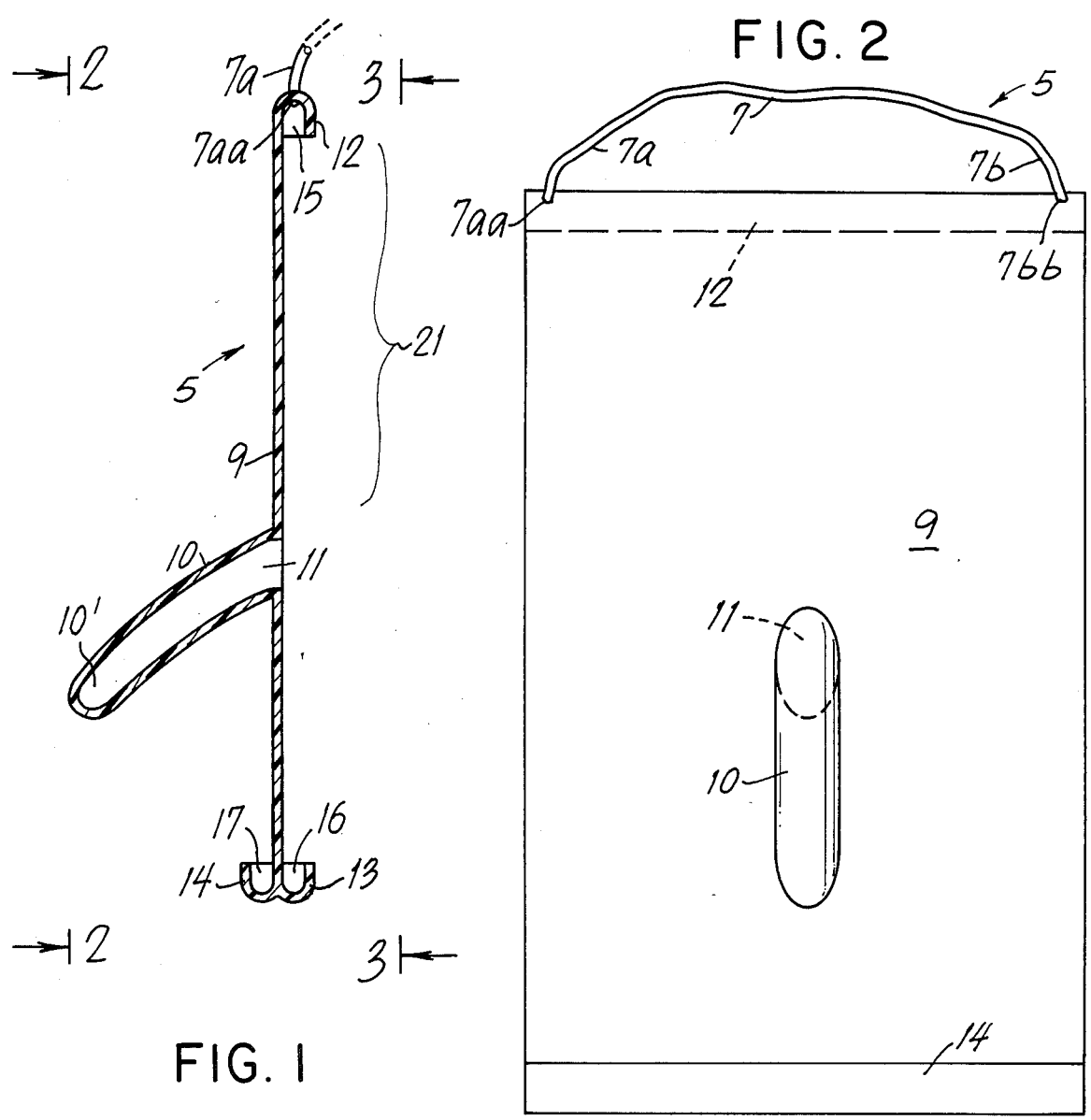
FIG. 2
FIG. 1
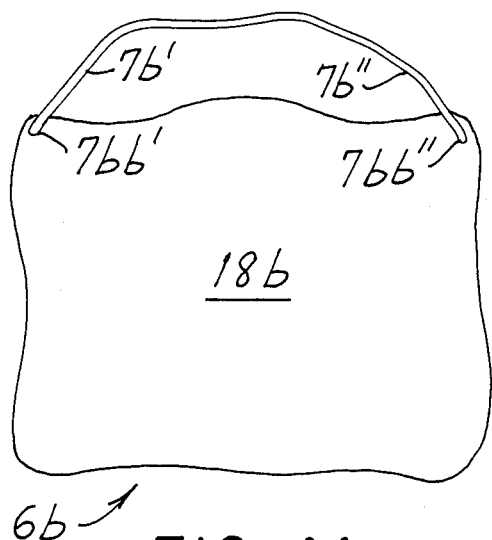
FIG. 4A

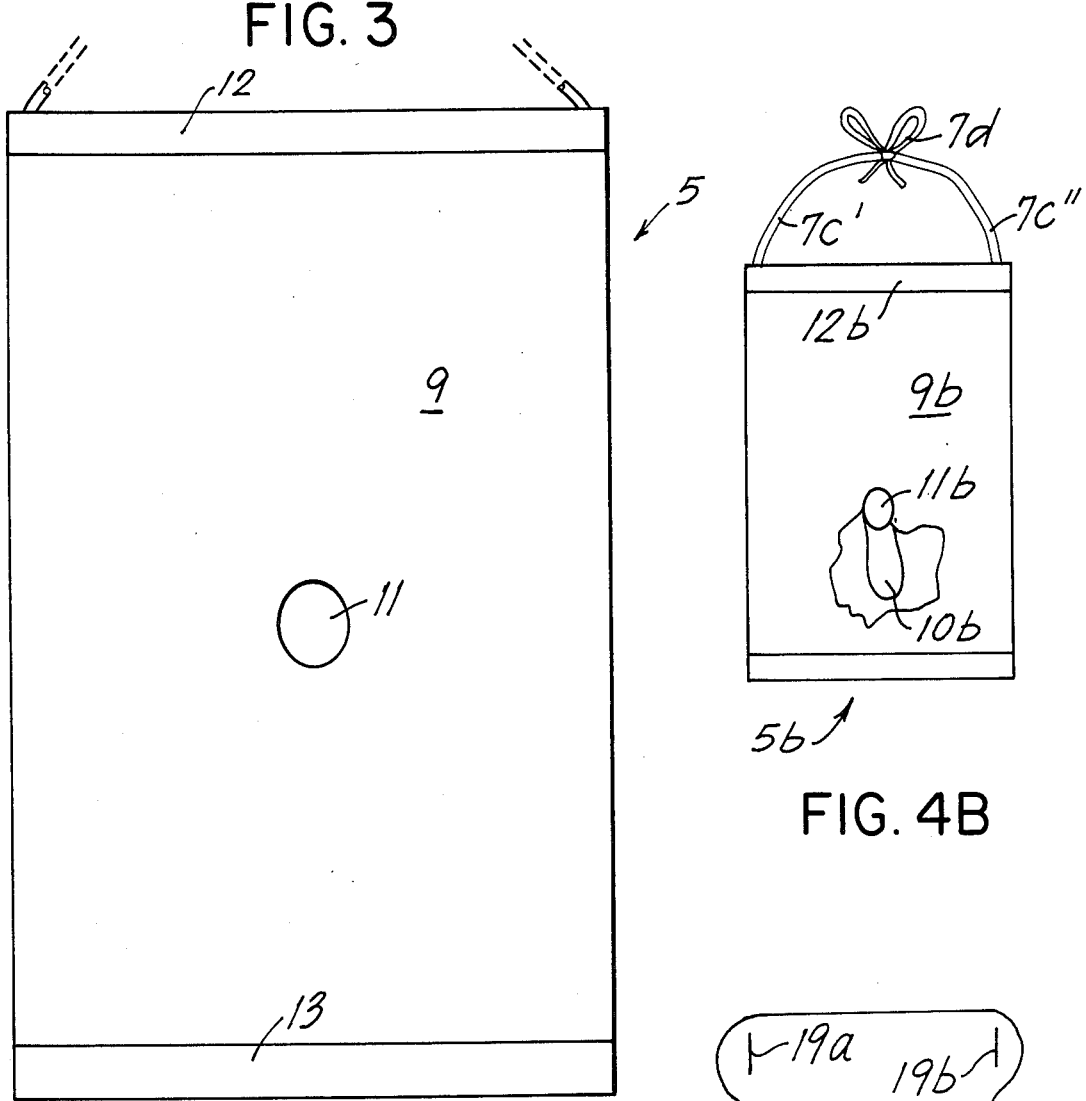
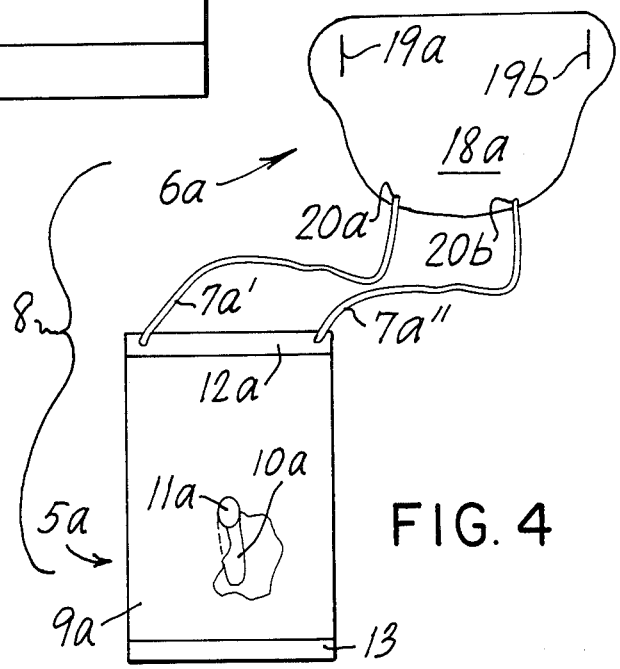

AIDS-PREVENTING CONDOM SHIELD ARTICLE

This invention is directed to a novel disease-prophylactic sex-device in the nature of an improved condom reducing potential risk of acquiring one or more diseases during copulation.

BACKGROUND OF THE INVENTION

1. Field of Invention

Prior to the present invention there have been throughout history a multitude of devastating venereal diseases spread as a result of intimate contact between male and female humans, particular through copulation and/or kissing, such as syphilis, gonorhea, herpes, and the like. The most recent scourge, equated with the severity of the Black Plague, is the venereal disease commonly known as aids, resulting in devastation of not only those who are involved in extra-marital copulations and/or kissing, but transmitted accidentally by blood and/or unsteril needles during even authorized vaccinations and/or blood transfusions and the like, after which the infected innocent(s) transmit(s) the aids to his/her spouse. AIDS can be spread even by water or tears and/or saliva from an infected person (see newspaper NEWSDAY, Aids/NY, Feb. 3, 1987, "THE SURGEION GENERAL'S REPORT"/p.5. Thus, the spread is not limited to the drug users of dirty needles nor to those practicing extramarital sex. In any event, for one and all, it has already been publically stated that at least a major way of averting or avoiding contraction of aids (and other venerial diseases) is to abstain from sex and kissing with at-least high-risk partners.

In light of a major degree of the transmissions of aids being between drug-users who concurrently practice indiscriminate natural and/or unnatural sex acts between members of the opposite and/or same sex-gender while under the influence of drugs, it is highly unlikely that there will be "abstainance" in these group(s) of persons.

Accordingly, there has been and is presently a concerted campaign to encourage the use of condoms, if persons insist and persist in practing particularly high-risk sex and/or kissing. However, to use such condoms as presently exist, while better than nothing, leaves open considerable and major risk of infection by and contration aids as a result of sloppy, careless and/or accidental smearing and/or spilling of copulation fluids from one or more of the sex partners, apart from the potential mixing of saliva. In any event, the great publicity and the common knowledge now a part of the public community, has made even the high-risk groups aware of the need of exercising greater care to prevent contraction of aids if they do not already have it. As well, those of less high-risk groups are aware that discretion and care are important even to them during this time of the great aids epidemic.

2. Related Prior Art

As to prior art, based upon a search of prior art patents prior to filing application for patent, nothing of relevance was found. Typical condom patents include Hogin U.S. Pat. No. 4,354,494 granted Oct. 19, 1982 and Pinranx U.S. Pat. No. 4,432,357 granted Feb. 21, 1984, both classified in International class A61F 5/4 and U.S. Class 128, subclass 294. A principal class searched also included A28, subclass 132r. Typical other non-relevant classes searched included A28, subclass 132r. Typical other non-relevant U.S. patents located, out of about 155 U.S. patents turned-up by computer search, the numbers of which were: U.S. Pat. Nos. 4,576,156 to a prophylactic device and method; and 4,566,458 to a thorax protector; and 4,526,578 to a vaginal diaphragm; and 4,499,154 to a dipped rubber article; and 4,492,220 to a vaginal speculum protector; and 4,450,836 to a custom valved cervical cap with deformable margin; and 4,446,860 to devices and methods for the prevention of transmission of veneral disease and non-gonocal genital infections; and 3,881,477 to a fluid discharge appliance for maintaining a sterile enclosure; and 3,452,302 to a vaginal bib.

OBJECTS

Objects of the invention include the overcoming and/or avoiding one or more problems of the type(s) described above.

Another object is more particularly to obtain a disease-prophylactic sex device or article the use of which will likely avoid the contraction and/or spreading of aids by kissing and/or copulation.

Another object of the present invention is to limit the co-mingling and/or contact of infected surfaces and/or fluids thereof between potentially infected person(s) and non-infected person(s) during acts of copulation and/or kissing.

Another object is to reduce the possiblity of accidental contact between infected and noninfected person(s) and/or their fluids during and after the act(s) of copulation.

Other objects become apparent from the preceding and following disclosure.

One and more objects of this invention are obtained by the invention as described and claimed herein.

SUMMARY OF THE INVENTION

Broadly the invention may be described as a disease-prophylactic sex-device or article, and a combination in a preferred embodiment, as follows.

The is provided an elongated water-imperious sheet having a normally flat (or substantially planar) face (surface) and having an opposite face that is likewise normally flat, with the height thereof between the upper (top) and lower (bottom) ends thereof and the width thereof between the left and right edges of the sheet. Normally about central of the width, and central or below central of the height of the sheet, there extends a close-end water-impervious sleeve-like structure from the above-noted opposite face, in the nature of a condom-structure that is an integral part (sealed against any potential leaking or ripping, tearing therefrom and/or bursting) of the sheet itself, as a continuous part of the sheet.

In a preferred embodiment, the length of the upper portion of the sheet's height, i.e. the portion above the hole of the sheet, extends a sufficient distance as to cover the navel of the male person wearing the condom-like sleeve, avoiding contamination and/or infection from body fluids often associated with normal and-/or diseased navel(s) of copulating person(s).

In a preferred embodiment(s) of the invention, there is/are one or more cup-like structures at position(s) beneath the hole toward the lower (bottom) end of the sheet, sealably mounted on (and/or a part of) the sheet itself, mounted and positioned such that any liquid(s) traveling by gravity or by rubbing or by other forces, toward the bottom of the sheet from the hole on the flat face and/or on the opposite face of the sheet, flow into and is/are captured (entrapped by) and retained by the cup-like structure(s), thereby avoiding fluid(s) from space within the sleeve-structure and/or hole and/or from an exterior surface of the condom-like closed-end sleeve, and/or from either the flat or opposite face, from being spread beyond a lower end of the sheet.

In further preferred embodiment(s), there is/are one or more fastening mechanisms and/or structure(s)-/element(s) by which at-least the upper end(s) of the sheets are temporarily (intermittently) secured to the body of the male person wearing the condom-like sleeve, typically securing around the waist and/or the neck, and or attached to another article that is secured.

In a still further embodiment, as a preferred combination, there is provided a mask-like element that is sheet-like in nature and is likewise water impervious, having a size and shape of sufficient height and width dimensions as to substantially cover the mouth and nose of a typical man. Attached thereto or a part thereof is/are one or more mechanisms for reasonably securing the mask onto the head of the person in the worn position during sex and/or copulation, in order to avoid the touching of lips and/or saliva of the opposite mouths of the copulating partners.

The distance between the hole and the bottom of the sheet is preferably at-least about two inches, more preferably about four or more inches, and the distance between the hole and the top of the sheet is preferably at-least two inches, and more preferably about seven or more inches, together with the width of the sheet including preferably at-least two inches on each side of the hole, more preferably four or more inches on each side of the hole, in order to further enhance the possibilities of total isolation of infected parts of the copulating bodies and fluids thereof.

The composition of the sheet and sleeve structure and liquid-retainer cup(s) may be made of any suitable and/or conventional plastic(s) and/or rubber (natural and/or synthetic) preferably having flexibility and/or reliency and/or at-least some physical capability to stretch, and sufficient tensil strength as to resist normal strains encountered and/or expected to be normally encountered during copulation between sex partners, i.e to resist ripping, tearing, bursting, or the like. Such conventional material are already in commercial use in the present manufacture of condoms.

In a more preferrred embodiment of the invention, the closed-end sleeve-like extension from the shield-sheet, is a continuing same unbroken-structure, initially molded as a single composition commonly-formed or otherwise produced as a part thereof, as opposed to being a separate sleeve subsequently fused or adhered or attached thereto.

THE FIGURES

FIGS. 1, 2 and 3 each represent a common embodiment of the invention, while

FIGS. 4, 4A and 4B each represent diffenent embodiments and variations and/or combination thereof.

More particularly, FIG. 1 illustrates a side view in partial cross-section, of the entire device, including a line or string 7a anchored at the top at one edge of the sheet, the string or line being shown in an inpart-view.

FIG. 2 is a view of FIG. 1 taken along lines 2—2 of FIG. 1, in elevation plan view of the opposite-flat face from which the closed-end sleeve extends, showing the entire top line and/or string and opposite ends thereof attached to the upper end of the sheet.

FIG. 3 likewise shows the embodiment of FIG. 1 as taken along lines 3—3 as an elevation plan view of the flat side in which the hole is defined.

FIG. 4 illustrates a preferred combination including the mask for covering the mouth and nose, the sheet and closed-end sleeve being shown and corresponding to the embodiment of FIGS. 1, 2 and 3; the FIG. 4 illustrates an elevation plan view, with partial cut-away, showing the flat face of the sheet having the hole therein.

FIG. 4A illustrates an alternate embodiment of the face mask with here a continuous eleastic mount, shown in front elevation plan view, for use in combination with a sheet and sleeve-structure embodiment such as that of FIGS. 1 through 3.

FIG. 4B illustrates another embodiment identical to that of FIGS. 1, 2 and 3, except for the separate strings or lines tied intermittently tied as a bow, shown in elevation plan view.

DETAILED DESCRIPTION

In greater detail, the Figures representing variations and greater combinations, are described utilizing related numbers (indicia) for elements of the same general structure and/or function.

With regard to FIGS. 1, 2 and 3, all to a common embodiment, there is disclosed the entire device (or article) 5, including the mounting structure 7 thereof having its opposite ends 7a and 7b mounted at points 7aa and 7bb (typically brads or line tied through holes, on top opposite edges of the sheet (shield) 9 of which the closed-end sleeve 10 extends forming tubular space communicating with the opening 11. The strap or line 7 may be and preferably is elastic, such that it may be placed around the waist or neck, and the length may be variable, and it optionally may be detachable at either or both ends thereof. At the lower end on the hole-side flat face, there is formed the cup-like structure 13 forming liquid-catching and retaining space 16 at the bottom end of the sheet 9. On the opposite face, likewise there is formed the cup-like structure 14 forming liquid-catching and retaining space 17. At the top end of the sheet 9 there is formed on the hole-side flat-face the handle or grasping element 12 having its finger-space 15, providing a convenient and handy place for two-finger grasping and handling the device or article after use, devoid of handling soiled or potentially soiled disease-carrying portions.

In FIGS. 4 and 4B, the same features are disclosed as for that of FIGS. 1, 2, and 3, except for the addition mask 18a having ear-mounting slits 19a and 19b, and line or string-mounting holes 20a and 20b at which the lines or strings 7a' and 7a" are attached as shown. For this combination of FIG. 4, the indicia 8 includes each of indicia (and elements thereof) 6a, 7a', 7a" and 5a, of which the indicia 6a referring to the mask 18a and its various elements above-described.

FIG. 4B illustrate an embodiment identical to that of FIGS. 1, 2 and 3, except that the attaching structure(s) are separate lines or straps or strings 7c' and 7c" intermittently tied typically as a knot or bow 7d.

Before engaging in sexual copulation, a male person would insert his penis into the space 10' of the closed-end sleeve 10 through the hole 11 and secure the elastic band 7 onto his body prior to engaging in sexual intercourse. Followng the completion thereof, the male person may grasp the handle-structure 12 while and in assisting removing and handling the entire device/article 5 prior to and during the disposal thereof. Thereby, he avoids contaminating his hands with copulation fluids from the female person.

During use, any copulation fluids of the man that may escape through the hole 11 and/or get onto the hole-side surface of the sheet 9, will be collected in the space 16 if they drain or are forced downwardly toward the bottom edge of the sheet 9. Likewise, any fluids escaping from the female during copulation, if they are deposited onto the sleeve-side of the sheet 9, will be captured and retained in the space 17 if they drain or are forced toward the bottom of the sheet 9.

The mask article 6 is mountable by inserting the ears through the slits 19a and 19b. FIG. 4A shows an alternte embodiment in which the elastic band having secured ends 7b' and 7b" secured at holes 7bb' and 7bb", is merely slipped onto the head, to mount the mask.

The mounting mechanism of either and/or both the mask and/or the condom-sheet may make use of any conventional and/or equivalent adhesive or other sticky tape, hooks and loops, or the like, as might be desired.

Another major advantage of the present invention lies in the simplicity of the invention and of manufacture and low cost of manufacture thereof, in contrast to the tremendous potential benefits to the users thereof, and of the simplicity of its use. The cost of manufacture of the article of this invention is about the same low cost as that of currently available and produced condoms, but with the greater protections of the present invention.

It is within the scope of the invention to make such variations and/or modifications and/or substitution of equivalents as would be obvious to a person of ordinary skill in this art.

I claim:

1. A disease-prophylactic sex-device comprising in combination: an elongated water-impervious sheet having a substantially flat face and an opposite side face, having a top-end and an opposite bottom-end forming a height therebetween, having a right-edge and an opposite left-edge forming a width therebetween, and having a hole formed therein on said substantially flat face of the sheet at a location intermediate between said top end and said opposite bottom end of said height and between said left edge and said right edge of said width; a water-impervious closed-end sleeve extending from and integral and continuous with said opposite-side face of the sheet forming said hole on said flat face, said water-impervious sheet and said elongated water-impervious sleeve jointly comprising a unified single composition commonly-formed as a continuing unbroken-structure thereby water-impervious such that it is sealed against any potential leaking therethrough, said closed-end sleeve having opposite interior and exterior surfaces and being shaped as and functioning as a condom and forming free-space therein in communication with said hole, such that when a mans's sex organ is inserted and positioned therein, the sex organs of the man and of a female during copulation are segregated by the closed-end sleeve and said sheet is avoided; and at-least one cup-like means formed at a position spaced-below said closed-end sleeve and said hole formed thereby, each said cup-like means being positioned and adapted to collect and retain any liquid that has moved or been forced from said exterior or interior surface of said closed-end sleeve or from said hole and said free-space, toward said bottom into said cup-like means.

2. A disease-prophylactic sex-device of claim 1, in which said at-least one cup-like means includes a first cup-like structure formed on said substantially flat face in juxtaposition to said bottom-end.

3. A disease-prophylactic sex-device of claim 2, in which said at-least one cup-like means includes a second cup-like structure formed on said opposite face in juxtaposition to said bottom-end.

4. A disease-prophylactic sex-device of claim 3, in which said width of said sheet is at-least about four inches between said right-edge and said left-edge, and in which said closed-end sleeve and said hole formed thereby are each positioned substantially centrally of said width.

5. A disease-prophylactic sex-device of claim 4, in which a first height-distance between said hole and said bottom end is at-least about two inches, and in which a second-height distance between said hole and said top-end is at-least about two inches.

6. A disease-phophylactic sex-device of claim 5, in which said second-height distance is at-least about seven inches sufficiently to overlay a navel of a male person wearing said closed-end sleeve as a condom.

7. A disease-prophylactic sex-device of claim 6, including a securing means for anchoring said top-end onto a mid-body or upper-body portion of a male person wearing said closed-end sleeve as a condom.

8. A disease-prophylactic sex-device of claim 1, in which said at-least one cup-like means includes a cup-like structure formed on said opposite face in juxtaposition to said bottom-end.

9. A disease-prophylactic sex-device of claim 3, in which a first-height distance between said hole and said bottom end is at-least about two inches, and in which a second-height distance between said hole and said top-end is at-least about two inches.

10. A disease-prophylactic sex-device of claim 9, including a water-impervious mask having attaching means for the mounting thereof over a mouth and a nose of a man wearing said said closed-end sleeve as a condom.

11. A disease-prophylactic sex-device of claim 6, including a handle-means in juxtaposition to said top-end, extending from said flat-face, for manually grasping, positioned at a location away from contact with said opposite-side face.

12. A disease-prophylactic sex-device of claim 2, including a securing means for anchoring said top-end onto a mid-body or upper-body portion of a male person wearing said said closed-end sleeve as a condom.

13. A disease-prophylactic sex-device of claim 12, including a water-impervious mask securable over a mouth and a nose of a man wearing said closed-end sleeve as a condom, by said securing means.

14. A disease-prophylactic sex-device of claim 2, as a kit including a water-impervious mask securable over a mouth and a nose of a man wearing said closed-end sleeve as a condom, and including securing means for mounting said mask over a man's mouth and nose.

15. A disease-prophylactic sex-device of claim 14, including a handle means for manual grasping, said handle means being positioned at a location away from contact with said opposite-side face and positioned in juxtaposition to said top-end of said sheet, extending from said flat-face.

16. A disease-propylactic sex-device of claim 2, including a handle-means in juxtaposition to said top-end, extending from said flat-face, for manually grasping, positioned at a location away from contact with said opposite-side face.

* * * * *